United States Patent [19]

Eklund et al.

[11] Patent Number: 4,932,806
[45] Date of Patent: Jun. 12, 1990

[54] COMPLIANT JOINT

[75] Inventors: Wayne D. Eklund, Edgewood; James J. Kerley, Greenbelt, both of Md.

[73] Assignee: The United States of America as represented by the Administrator of the National Aeronautics and Space Administration, Washington, D.C.

[21] Appl. No.: 326,863

[22] Filed: Mar. 21, 1989

[51] Int. Cl.$^5$ ............................................. F16D 3/02
[52] U.S. Cl. ................................... 403/57; 403/113; 403/291; 464/56; 464/132
[58] Field of Search ..................... 403/57, 58, 53, 74, 403/291, 220, 152, 113, 79, 112; 464/56, 136, 132, 55, 119; 901/29, 28

[56] References Cited

U.S. PATENT DOCUMENTS

| | | | |
|---|---|---|---|
| 899,534 | 9/1908 | Hoffmann | 464/132 X |
| 1,408,475 | 3/1922 | Schaap . | |
| 1,659,353 | 2/1928 | Dwyer | 464/56 |
| 1,695,116 | 12/1928 | Lord | 403/58 X |
| 2,765,930 | 10/1956 | Greer et al. . | |
| 2,822,550 | 2/1958 | Grodzki . | |
| 3,087,313 | 5/1963 | Kerley . | |
| 3,204,943 | 7/1965 | Kerley . | |
| 3,238,743 | 3/1966 | Burroughs | 464/56 |
| 3,238,744 | 3/1966 | Camossi | 403/291 X |
| 3,238,745 | 3/1966 | Burroughs | 464/56 |
| 3,844,663 | 10/1974 | Prette . | |
| 4,202,107 | 5/1980 | Watson . | |
| 4,494,417 | 1/1985 | Larson et al. . | |
| 4,512,679 | 4/1985 | Petrzelka et al. | 464/132 X |
| 4,655,778 | 4/1987 | Koeneman . | |

Primary Examiner—Andrew V. Kundrat
Assistant Examiner—Peter M. Cuomo
Attorney, Agent, or Firm—R. Dennis Marchant; John R. Manning; Alan J. Kennedy

[57] ABSTRACT

A compliant joint is provided for prosthetic and robotic devices which permits rotation in three different planes. The joint provides for the controlled use of cable under motion. Perpendicular outer mounting frames are joined by swaged cables that interlock at a center block. Ball bearings allow for the free rotation of the second mounting frame relative to the first mounting frame within a predetermined angular rotation that is controlled by two stop devices. The cables allow for compliance at the stops and the cables allow for compliance in six degrees of freedom enabling the duplication or simulation of the rotational movement and flexibility of a natural hip or knee joint, as well as the simulation of a joint designed for a specific robotic component for predetermined design parameters.

18 Claims, 4 Drawing Sheets

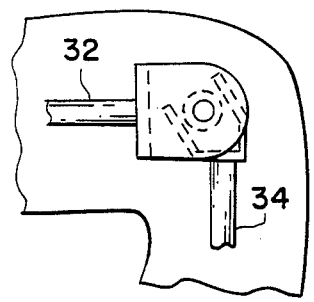
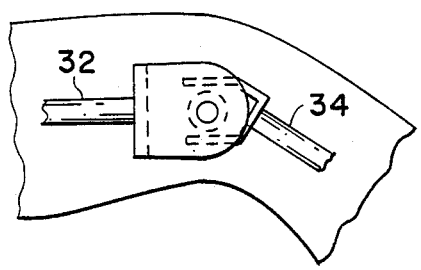
FIG. 6a
FIG. 6b
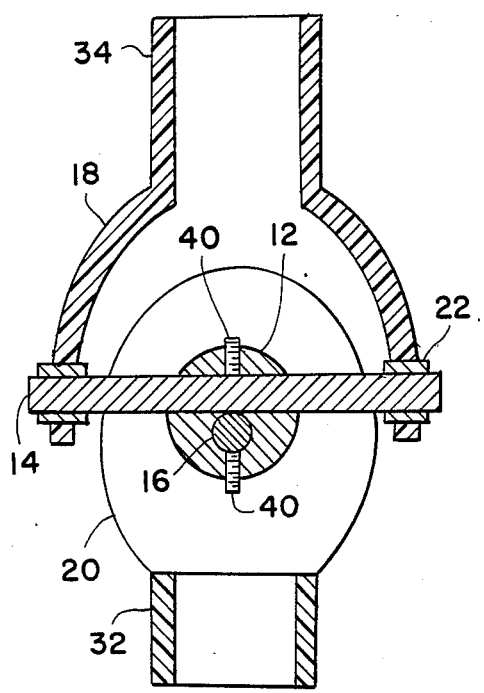
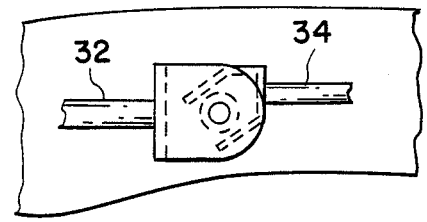
FIG. 6c
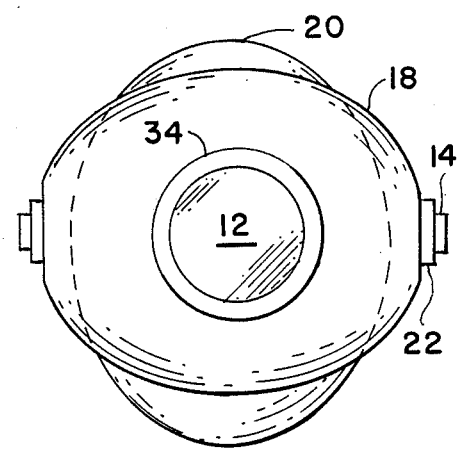
FIG. 7a
FIG. 7b

COMPLIANT JOINT

ORIGIN OF THE INVENTION

The invention described herein was made in the performance of work under a NASA contract and by an employee of the United States Government and is subject to the provisions of Section 305 of the National Aeronautics and Space Act of 1958, Public Law 85-568 (72 Stat. 435; 42 U.S.C. 2457), and may be manufactured and used by or for the Government for governmental purposes without the payment of any royalties thereon or therefor.

TECHNICAL FIELD

The invention relates to a compliant joint for prosthetic and robotic devices which permits rotational movement in three different planes and more specifically to a joint that provides for the controlled use of cable segments coupled into a common mounting joint.

BACKGROUND ART

In the field of robotic devices there is a need for joint structures that connect robotic limbs or components that will permit precision controlled rotation in three planes. This is also a desirable feature for joint prosthesis for replacing a diseased or damaged joint between human body skeletal members where the joint prosthesis should simulate the durable and resilient characteristics of the joint it replaces as well as duplicate the rotational movement and flexibility of the replaced joint.

There are numerous prior art devices that disclose prostheses for the replacement of knee, elbow, hip and knuckle joint but problems have been encountered with each type of design. Usually the joint prostheses have hinging elements formed with metal-to-metal or metal-to-plastic bearing elements such that insufficient resiliency or flexibility is provided at the hinging element to cushion and absorb impact loads or lateral and compressive loads that are applied to the joint in every day use. Thus, the joints eventually fail and have to be replaced.

To combat the problem of insufficient resiliency or flexibility some devices have been proposed in which the prosthesis is formed almost entirely of a flexible member such as an elastomer. Problems have occurred here in that shear forces over a period of time cause the elastomer to tear resulting in the eventual failure of the prosthesis. Also if the elastomer is too flexible or becomes more flexible due to prolonged use, the skeletal components have sometimes become dislocated resulting in failure.

For robotic devices there are other problems. Conventional robot arms are built up from a number of elements and joints, which besides the tool and the load also must support the equipment for the motion and power generation for the separate elements. This equipment usually comprises pneumatic or hydraulic cylinders, electric motors etc., which means that the elements and the joints have to be relatively coarse or heavy in order to support the equipment. Thus the robot will have a bulky shape and comparatively large external dimensions, which will reduce the flexibility of the robot arm.

There are robotic couplings available that use cable but there do not appear to be any in the prior art that disclose the controlled use of the cable to allow precise and predetermined control of the compliance flexibility and rotational movement of the robotic joint in three planes, as well as absorb heavy loads.

STATEMENT OF THE INVENTION

Accordingly, it is an object of the invention to provide a compliant joint that is flexible or compliant.

It is yet another object of this invention to provide a compliant joint with a high level of damping.

It is still another object of the invention to provide a compliant joint for a robotic applications having a high load capability.

It is another object of this invention to provide a compliant joint that allows for rotation in all three planes.

It is also an object of this invention to provide a compliant joint that is very durable and inexpensive to manufacture.

It is still a further object of this invention to provide a compliant joint prosthesis that can be utilized to replace a diseased or damaged joint for human body skeletal members that has the capability of simulating the movement and flexibility of the replaced body joint.

These and other objectives are accomplished in a compliant joint for robotic devices or a human skeletal joint prosthesis in which two U-shaped mounting brackets, which are coupled to robotic body components or skeletal body members, are mounted substantially perpendicular to one another by means of swaged cables that interlock at a center block. Ball bearings allow for free rotation of the second bracket relative to the first bracket within a predetermined angular rotation that is controlled by two stop devices. Cable segments provide for compliant or more damped rotation of the brackets at the stop devices and in other planes of rotation. By properly controlling variables such as cable size, cable length, cable stranding, cable pretwisting, and cable material, the degree of compliance within the cables can be controlled which will allow for the adjustment of flexibility in three planes for any joint. Thus, the rotational movement for a knee or hip joint can be substantially simulated for a joint prosthesis.

BRIEF DESCRIPTION OF THE DRAWINGS

In the drawings like parts are designated by the same references.

FIGS. 6a, 6b and 6c show a modified version of the offset compliant joint shown in FIGS. 5a and 5b shown in three varying positions.

FIGS. 7a and 7b show a special embodiment of the compliant joint for mounting applications where mounting space is limited.

DETAILED DESCRIPTION OF THE INVENTION

Figure 1:
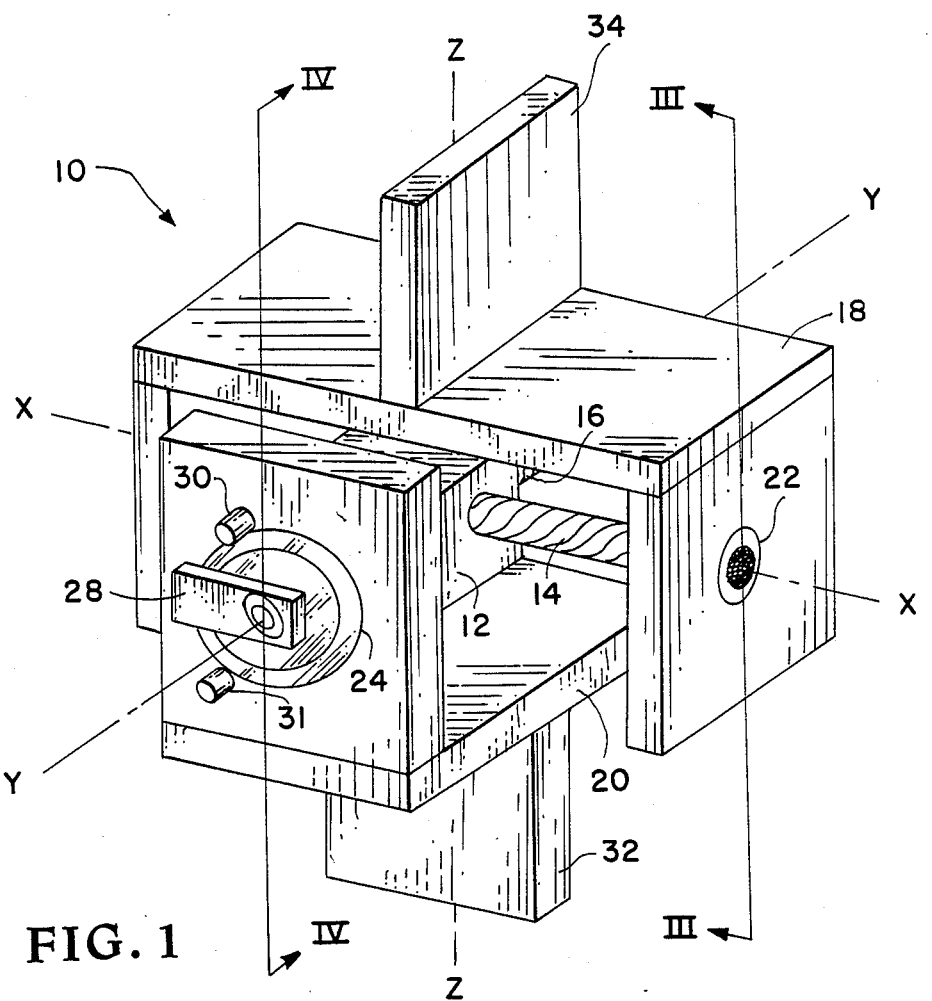
FIG. 1 is a pictorial perspective view of the compliant joint.
Figure 2:
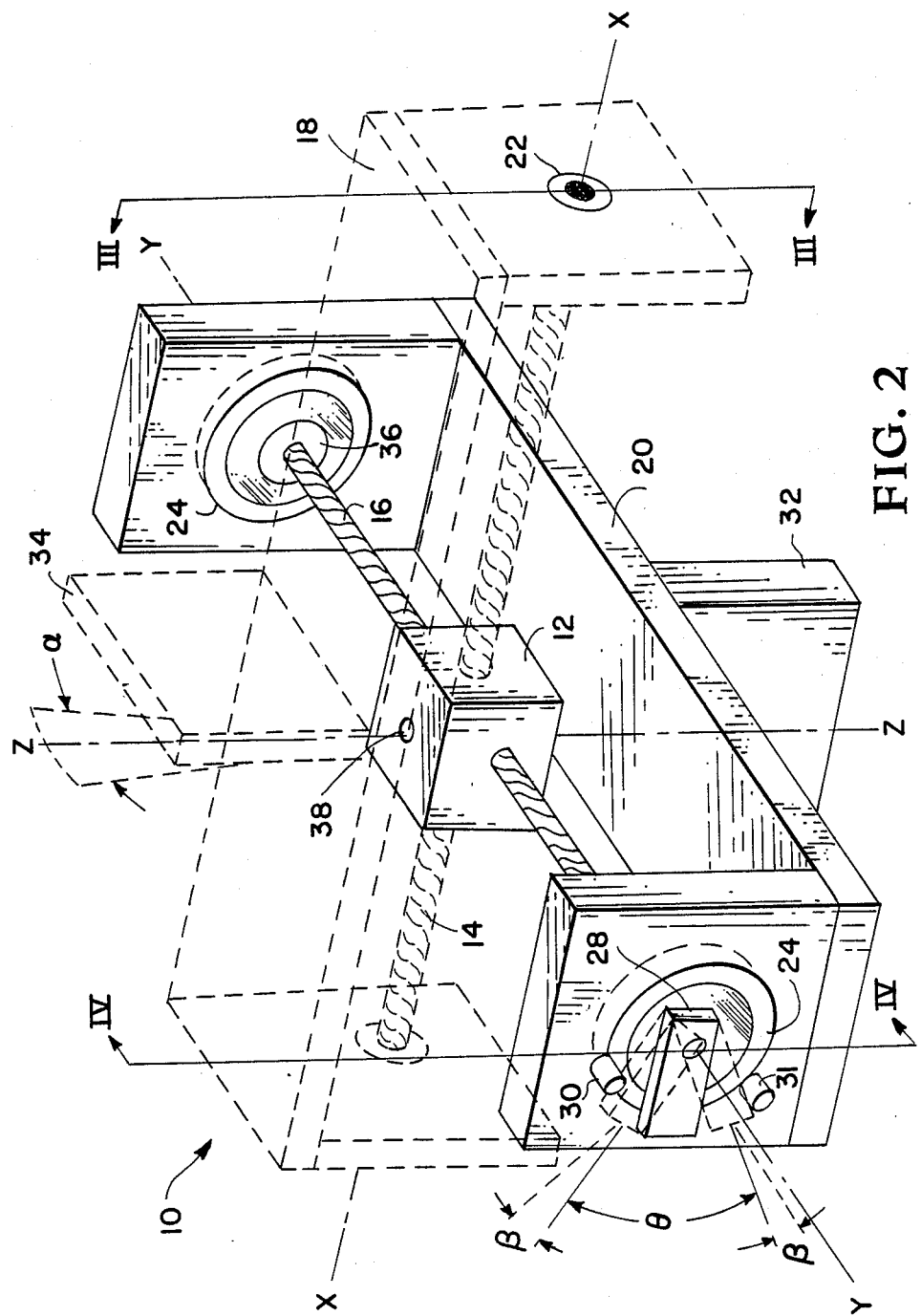
FIG. 2 is an exploded view of the knee joint as shown in FIG. 1.

The compliant joint 10 is shown generally in FIG. 1 and in the exploded view in FIG. 2. A center piece 12 is preferably shown at the center of the compliant joint 10.

The center piece 12 is shown as a cubic-shaped element in the embodiment shown in FIGS. 1 and 2; however, it could be spherical or other geometric shapes depending upon its usage.

Extending through center piece 12 are cables 14 and 16. Cables 14 and 16 pass through center piece 12 at substantially right angles to one another. The cables 14 and 16 shown are preferably metal such as stainless steel or any metal that can be spun into cable. The cable can be regular lay cable or Lange lay cable; however, it is important that the cables be independent wire rope core (IWRC). The ends of cable 14 are joined to "U" shaped bracket 18 by swaging the ends of the cable 14 to end swage 22. The ends of cable 16 are joined first to bearings 24 using bearing clamp 26 or they can be joined to the bearing 24 by swaging. Bearing 24 is in turn mounted onto a second "U" shaped bracket 20. Bearing 24 has a stop arm 28 or rod-like member positioned so that stop arm 28 can rotate back and forth between stops 30 and 31. End grip 32 extends from the outer surface of "U" shaped bracket 20, and a second end grip 34 extends from the outer surface of "U" shaped bracket 18. The end grips 32 and 34 are shown broadened out so as to connect to a flat surface such as a robotic machine element, but they could be smaller and round-shaped so that the end grips could connect to the center of a bone for a knee or elbow joint as will be discussed later.

FIG. 2 illustrates an exploded view of the compliant joint 10 that can be used for a knuckle, knee, hip or elbow joint. This joint is used where free rotation is needed through certain degrees of motion in one plane, but at the same time there is compliance in all degrees of rotation. This allows the joint to absorb large loads in any of the three-dimensional planes and at the same time have the ability to demonstrate or possess the characteristic of easy motion and compliance in the other planes. The free motion is shown as the region of rotation or angle $\theta$, which shows the range of movement or rotation for arm 28 which is allowed to rotate back and forth between stops 30 and 31. The rotation here is described as free rotation because arm 28 is attached to bearing 24 which reduces a substantial amount of the resistance caused by friction. Angles $\alpha$ and $\beta$, however, are representative of the region of compliant motion or rotating that is allowed because of this unique arrangement of cables 14 and 16. After arm 28 rotates through its maximum range of free movement and comes into contact with stop 30 or 31 depending upon the direction of rotation, the end grip 32 can yet rotate further through angle $\beta$ because of the compliant characteristic of cable 16. This movement is much more damped than is the movement that occurs during angle $\theta$ and the degree of compliance or damping can be controlled or varied by varying cable segment lengths, cable diameter, and cable stranding, pretwisting the cable, and/or changing the cable material.

End grip 34 which is mounted to U-shaped bracket 18 rotates through angle $\alpha$. Since cable 14 is not mounted to a bearing system such as bearing 24, there is no free motion or angle of free rotation $\theta$ for end grip 34. Thus, only compliant movement is demonstrated or allowed for end grip 34 as shown in this embodiment, because it simulates the movement in a knee, hip, elbow or finger joint where free movement is desired only in one plane. Yet, some degree of compliance is required to simulate the flexibility of a human joint in the other two planes.

Figure 3:
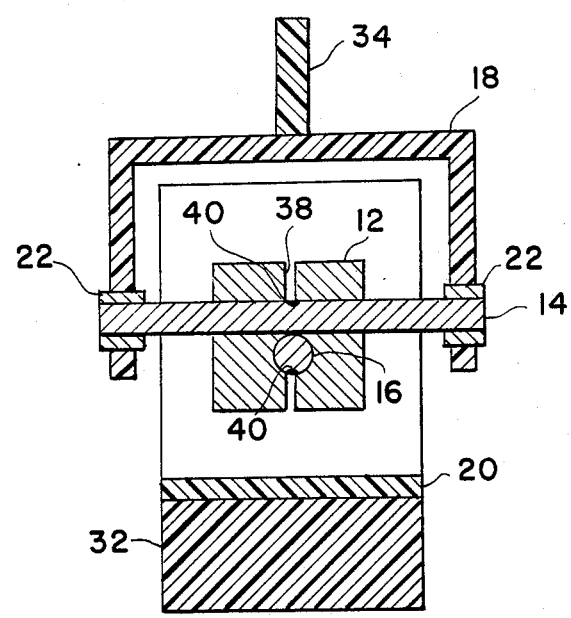
FIG. 3 shows a cross-sectional view along III—III as shown in FIGS. 1 and 2.

FIG. 3 shows a cross-sectional view III—III of FIG. 1 and FIG. 2 illustrating in more detail how cables 14 and 16 are connected to center piece 12 and how cable 14 is connected to mounting bracket 18. The ends of cable 14 are connected to mounting bracket 18 by means of end swage 22. The swage material could be soft silver, gold, platinum or copper depending upon the utilization of the compliant joint and the budget of the manufacturer. It should be noted that copper was preferred for this design. The same swage joint could be used for connecting the cable 14 and connecting mounting bracket 18, either swaged individually or together. It should be noted that the swaging techniques used for these joints are not those commonly used in cable fittings such as those used for slings and ship rigging. The cables used for the compliant joint are subjected to less force because they are not used in applications in tension but rather are used in applications in shear and rotation. The cable itself can be regular lay independent wire rope core (IWRC) or Lange lay (IWRC). The cable in the single strand can be regular lay going to the right side of center piece 12 and Lange lay going to the left side of center piece 12; however, in this case two additional swages would be required at junction 40. Center piece 12 would have to be adapted for this center swage connection. Junction 40 shows a swage of cable 14 (topside) and cable 16 (bottom side) to prevent rotation or slippage of said cables. This center swage could be performed with a pin, or a set screw, (not shown) or by making the center piece 12 out of steel driving a piece of copper through hole 38 to hold the cable in place. The preferred solution would be to thread hole 38 and use a set screw (not shown) to swage the cable. It should be noted that the center 40 of center piece 12 is the junction at which the cable segments would meet. If the center of rotation of the cable segments going to the left and right of the junction 40 cannot be in the same direction, then four pieces of cable segments would be required, and accordingly four swage connections would be necessary.

Figure 4:
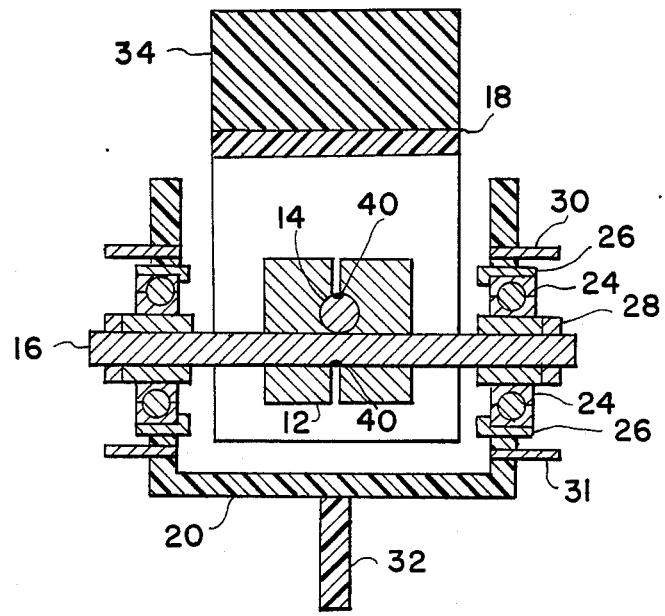
FIG. 4 shows a cross-sectional view along IV—IV as shown in FIGS. 1 and 2.

FIG. 4 shows a cross-sectional view IV—IV of FIG. 1 and FIG. 2 illustrating in more detail how cables 14 and 16 are connected t center piece 12 and how cable 16 is connected to bearings 24 and mounting bracket 20. This view shows bearing 24, and the rotational arm 28 and rotational stops 30 and 31 for rotational arm 28. There are two bearings 24, two rotational arms 28 and four rotational stops shown in FIG. 4. It should be noted that it is possible to have only one bearing located at one end of cable 16 and a swage (with no bearing) at the opposite end of cable 16 for special kinds of hinge action.

The bearings 24 can be of various types such as ball bearings, roller bearings or friction bearings; however, the bearing 24 shown in FIG. 4 is a ball bearing, which has been tested successfully. The type of bearing required will be dictated by the utilization of the compliant joint whether it be a human skeletal body joint or joint for robotic applications. The bearing can be captured by the same material (copper, gold, silver or platinum) that is used to swage the cable. If copper is used, then the copper is first swaged to the cable and the end is left free to move up. Then cable 16, center piece 12 are positioned in place and the same copper is utilized to hold the assembly to the bearing. The other end of the bearing can be attached to mounting bracket 20 with the same swaging material. Another method for attaching the cable 16 to bracket 20 or bearing 24 would be to use a form of silver solder with a tensile strength of approximately 20,000 psi. This kind of silver solder has been successfully used; however, the temperature of the cable has to be carefully controlled and the depth of the temperature along the cable has to be controlled to keep the silver solder and any other strong solders from flowing along the cable.

The shearing strength of the joint is controlled by the diameter, stranding, and material composition of the cable 16, and the width of center piece 12. Center piece 12 can be carefully drilled to receive a precise diameter of cable and create a specific shearing boundary for the cable; thus, a quarter inch diameter steel cable could withstand a shearing load in excess of 1,000 pounds. The length of the cable hole in center piece 12 also must be used to control the degree of compliance. There must be a balance between cable diameter and width of center piece 12 to achieve a designated shearing force in conjunction with a designated compliance. A compliant joint for a human body should be subjected to small shear loads thus small diameter cable can be used, but in robotic applications where substantial loads have to be supported, larger diameter cables will be required.

Figure 5A:
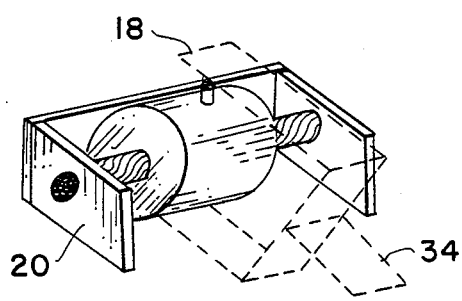
FIGS. 5a and 5b show another embodiment of the compliant joint with the center of rotation in an offset position.
Figure 5B:
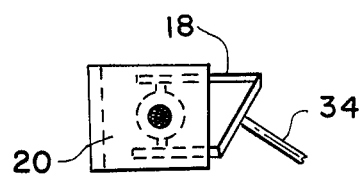

FIGS. 5a and FIG. 5b show another embodiment of the compliant joint which allows for the center of rotation of the compliant joint to move during rotation. Here a special angle is imposed on U-shaped bracket 18 causing end grip 34 to be in an offset position. This offset embodiment is most important for knee and elbow joints.

FIGS. 6a, 6b and 6c illustrate a modified version of FIGS. 5a and b showing three positions of a knee joint during rotation. The center of rotation of the knee is controlled showing the knee bent at a right angle in FIG. 6a, slightly flexed or bent in FIG. 6b, and knee joint fully extended or in a straight leg position in FIG. 6c. End grips 32 and 34 are shown as being round shaped and that they could enter the center of the bone; however, end grips 32 and 34 could be flat shaped for robotic applications. End grips 32 and 34 could be mounted in the skeletal body or in the robotic applications by threading the connecting members and screwing the parts together or they could be connected by a snap lock mechanism.

FIGS. 7a and 7b show a special embodiment of the compliant joint for a knee, elbow, finger, hip or robotic joint where mounting space is small and the end grips 32 and 34 are adapted for a special fitting. Note that center piece 12 is now spherical. End grips 32 and 34 are shown in such a way as to be fastened by threading, or they could be slide fitted over component parts, or they could be made to slide fit in the center of a special joint such as a bone. Note also that the mounting brackets 18 and 20 have an elliptical shape in this embodiment.

While the compliant joint of the present invention has been described in considerable detail, it is understood that various changes and modifications may occur to persons of ordinary skill in the art without departing from the spirit and scope of the invention as defined in the appended claims.

We claim:
1. A compliant joint for joining robotic body components or skeletal members such as knee, elbow, hip or finger joints, comprising:
   a center mass means,
   first and second U-shaped brackets surrounding said center mass means said first and second U-shaped brackets coupled to adjacent component means such as robotic components or skeletal members;
   a first pair of diametrically opposed cable segments coupled to opposite sides of said center mass means at one end of said cable segments, and coupled individually to legs of said first U-shaped bracket at the opposite end of said cable segments;
   a second pair of diametrically opposed cable segments coupled to opposite sides of said center mass means at one end of said cable segments, and coupled to individually to legs of said second U-shaped bracket at the opposite end of said cable segments, wherein the points of coupling of said cable segments to said center mass means lie in the same plane, and said points of coupling of said cable segments to said center mass means are perpendicular to adjacent points of coupling, thereby enabling said first and second U-shaped brackets with the ability to move angularly, vertically, laterally, and rotationally with respect to one another;
   bearings mounted onto said legs of said first U-shaped bracket, said bearings being coupled to said cable segment ends coupled to said first U-shaped bracket to allow for easier rotation of said second U-shaped bracket with respect to said first U-shaped bracket; and
   stop means incorporated into said bearings to limit the rotational movement of said second U-shaped bracket with respect to said first U-shaped bracket.

2. The compliant joint of claim 1, wherein said ends of said first and second pair of cable segments are coupled by swaging said ends to said center mass and said first and second U-shaped brackets.

3. The compliant joint of claim 1 wherein said bearings are ball bearings.

4. The compliant joint of claim 1 wherein the compliance in said cable segments can be varied by pre-twisting said cable segments in a clockwise or counterclockwise direction.

5. The compliant joint of claim 1 wherein the compliance in said cable segments can be varied by increasing or decreasing the diameter of said cable segments.

6. The compliant joint of claim 1 wherein the compliance in said cable segments can be varied by increasing or decreasing the lengths of said cable segments.

7. The compliant joint of claim 1 further including means for offsetting the position of attachment of at least one of said means for coupling U-shaped brackets to said robotic components or skeletal member.

8. The compliant joint of claim 1 wherein each cable segment of said pair of cable segments is maintained at a predetermined degree of compliance that may be different from said other cable segment.

9. The compliant joint of claim 1 wherein said bearings are friction bearings.

10. The compliant joint of claim 1 wherein said stop means comprises a arm mounted onto said bearing member wherein said arm rotates between two stop elements thereby limiting the rotational movement of said bearing.

11. A complaint joint for joining robotic body components or skeletal member such as knee, elbow, hip or finger joints comprising:
   a center mass means;
   first and second U-shaped brackets surrounding said center mass means said first and second U-shaped brackets coupled to adjacent component means such as robotic body components or skeletal members;

a first cable segment extending through and coupled to said center mass means and coupled at each end to each leg of said first U-shaped bracket;

a second cable segment extending through and coupled to said center mass means and coupled at each end to each leg of said second U-shaped bracket;

bearings mounted onto said legs of said first U-shaped bracket, said bearings being coupled to said cable segment ends coupled to said first U-shaped bracket to allow for easier rotation of said second U-shaped bracket with respect to said first U-shaped bracket;

stop means incorporated into said bearings to limit the rotational movement of said second U-shaped bracket with respect to said first U-shaped bracket; and means for offsetting the position of attachment of at least one of said means for coupling U-shaped brackets to said robotic components or skeletal member.

12. The compliant joint of claim 11, wherein the ends of said first and second cable segments are coupled by swaging said ends to said first and second U-shaped brackets.

13. The compliant joint of claim 11 wherein said bearings are ball bearings.

14. The compliant joint of claim 11 wherein the compliance in said cable segments can be varied by pre-twisting said cable segments in a clockwise or counterclockwise direction.

15. The compliant joint of claim 11 wherein the compliance in said cable segments can be varied by increasing or decreasing the diameter of said cable segments.

16. The compliant joint of claim 11 wherein the compliance in said cable segments can be varied by increasing or decreasing the lengths of said cable segments.

17. The compliant joint of claim 11 wherein said bearings are friction bearings.

18. The compliant joint of claim 11 wherein said stop means comprises a arm mounted onto said bearing member wherein said arm rotates between two stop elements thereby limiting the rotational movement of said bearing.

* * * * *